US008485195B2

(12) United States Patent
River et al.

(10) Patent No.: US 8,485,195 B2
(45) Date of Patent: Jul. 16, 2013

(54) DYNAMIC CRADLE, ESPECIALLY FOR TREATING HEAD AND NECK PAIN

(75) Inventors: Yaron Moshe River, Qiryat Tivon (IL); Tamir Levital, Haifa (IL)

(73) Assignee: Headway Ltd., Misgav (IL)

( * ) Notice: Subject to any disclaimer, the term of this patent is extended or adjusted under 35 U.S.C. 154(b) by 793 days.

(21) Appl. No.: 12/466,627

(22) Filed: May 15, 2009

(65) Prior Publication Data

US 2009/0272385 A1 Nov. 5, 2009

Related U.S. Application Data

(63) Continuation-in-part of application No. PCT/IL2007/001403, filed on Nov. 13, 2007.

(60) Provisional application No. 60/865,932, filed on Nov. 15, 2006, provisional application No. 60/929,435, filed on Jun. 27, 2007.

(30) Foreign Application Priority Data

Jul. 15, 2007 (IL) ........................................ 184624

(51) Int. Cl.
*A61F 6/06* (2006.01)

(52) U.S. Cl.
USPC ................ 128/830; 601/24; 601/25; 601/26; 601/39; 601/84; 601/86; 601/87; 600/587

(58) Field of Classification Search
USPC ............. 128/845, 869–870; 5/601, 622, 630, 5/632, 633; 602/17–18, 32–33; 378/204–205, 378/208, 20; 600/427, 587, 130; 601/23–26, 601/39, 84–87, 237, 240
See application file for complete search history.

(56) References Cited

U.S. PATENT DOCUMENTS

| | | | | |
|---|---|---|---|---|
| 3,188,079 | A * | 6/1965 | Boetcker et al. | 5/622 |
| 4,736,736 | A | 4/1988 | Moers et al. | |
| 5,320,641 | A | 6/1994 | Riddle et al. | |
| 5,456,655 | A | 10/1995 | Morris | |
| 6,971,997 | B1 | 12/2005 | Ryan et al. | |
| 2004/0171974 | A1 * | 9/2004 | Emsky | 602/33 |
| 2008/0104763 | A1 * | 5/2008 | Brown et al. | 5/636 |

FOREIGN PATENT DOCUMENTS

JP 5038307 A 2/1993

OTHER PUBLICATIONS

International Search Report published Apr. 16, 2009 for PCT/IL2007/001403 filed Nov. 13, 2007.
International Preliminary Report on Patentability published May 19, 2009 for PCT/IL2007/001403 filed Nov. 13, 2007.
Written Opinion published May 15, 2009 for PCT/IL2007/001403 filed Nov. 13, 2007.

* cited by examiner

*Primary Examiner* — Patricia Bianco
*Assistant Examiner* — Camtu Nguyen
(74) *Attorney, Agent, or Firm* — Marty Fleit; Paul D. Bianco; Fleit Gibbons Gutman Bongini Bianco PL

(57) ABSTRACT

The present invention discloses an apparatus for treating patient body or an organ thereof, especially his/her head and neck, by controllably maneuvering said treated organ, comprising; cradle adapted for holding said treated organ stably and comfortably; and, a maneuverable platform upon which said cradle rests, comprising maneuvering means adapted for rotating the platform in the Sagittal, Coronal, Horizontal planes or in any combination of the planes thereof for a predetermined duration; wherein said maneuver of said organ is characterized by parameters selected from the Allowed Movements. It is especially in the scope of the invention wherein the treated organ is maneuvered in a lobular three dimensional manner. The invention also discloses methods for treating patient body or an organ thereof by this apparatus; methods for decreasing HIT, MIDAS, VAS/NRS, NDI and EPS, and a method for increasing (S)MFA.

17 Claims, 6 Drawing Sheets

DYNAMIC CRADLE, ESPECIALLY FOR TREATING HEAD AND NECK PAIN

CROSS REFERENCE TO RELATED APPLICATIONS

This application is a continuation-in-part application of International Application No. PCT/IL2007/001403, filed 13 Nov. 2007, which claims priority to U.S. Provisional Application Nos. 60/865,932 (filed 15 Nov. 2006) and 60/929,435 (filed 27 Jun. 2007) and Israeli Patent Application No. 184624, filed 15 Jul. 2007. The entire contents of each of these applications are incorporated herein by reference.

FIELD OF THE INVENTION

The present invention generally relates to a dynamic cradle for prevention and treatment of neck and head pain.

BACKGROUND OF THE INVENTION

The invention relates to a dynamic cradle. An important salient feature of primary and secondary headache syndromes is muscle dysfunction. Furthermore other sources of pain have similar effects. Whatever the origin of pain, (trauma, pathology of the cervical spine, etc.) patients frequently develop lateral, anterior and posterior neck muscle shortening, over-contraction, and subsequent muscle hyperalgesia. This hyperalgesia or muscle spasm is a part of a vicious cycle mechanism. Neck mobilization and/or physical therapy are effective for some patients whereas in other patients biofeedback relaxation techniques are helpful. However, in many patients neither physical therapy nor biofeedback relaxation is effective. The use of a cradle or cradle for mobilization, which also uses biofeedback to inform its operation, would therefore seem an apt solution.

Korean patent 62631 describes an electromechanically powered device intended to facilitate movement and increase range of motion for stroke patients. This device would be included as part of prescribed physical therapy to enable stroke patients to exercise that would otherwise be unable to independently do so. The device is an automatic strength amplifier using the detected electromyograph (EMG) as an indication of residual muscle strength. In the case of a patient who is unable to move his/her arm, the addition of strength amplification allows him/her to perform standard physical therapy exercises. This device, while providing movement based on EMG feedback, is adapted for the movement of arms only. Thus treatment for relaxation of head and neck muscles is not provided.

U.S. Pat. No. 5,320,641 discloses a device for spinal rehabilitation, allowing a limited elevation/depression of different parts of the spinal column, not necessarily the cervical spine. The device allows only one degree of freedom, no true feedback from the patient. It mainly relates to post operative treatment and not for the treatment of headache and/or neck pain. It is mainly focused on enlarging the flexion/extension range of movement of the neck post trauma, post surgery.

Japanese patent 5,038,307 describes a seat for a vehicle having variable air pressure mats within. Electromyograph signals are taken of the driver's body. When these signals indicate that the driver is tired, the air pressure of the seat is varied. However this variation is not intended to relax the driver but rather to increase his level of alertness while driving. The pattern of inflation is therefore not adapted to decrease the electromyographic potentials indicating muscle tension by use of feedback. Since the head and neck are not specifically stimulated by this cradle, it is unlikely that the cradle is adapted to provide relief from headaches or muscle tension. It does not reposition the head and neck in a manner similar to physical therapy adjustment. Finally it does not determine the ideal degree of movement for each individual, nor does it maintain a computerized record of such.

Hence, a system for the computerized movement of viscous fluid or other flexible material pillow-like cradle forming a cradle around the head, using motors that move a platform holding the cradle, and also using electromyographic feedback and a computer algorithm to determine the optimum sequence, and tempo of movement that is adapted to provide maximum relaxation of the head and neck muscles, is still a long felt need.

BRIEF DESCRIPTION OF THE DRAWINGS

In order to understand the invention and to see how it may be implemented in practice, a plurality of embodiments is adapted to now be described, by way of non-limiting example only, with reference to the accompanying drawings, in which FIG. 1 schematically presents various possible rotations of the head about the 101 Sagittal, 102 Coronal, and 103 Horizontal planes;

FIG. 4*a* sketches the 3 planes of head and neck movement, together with the 3 axes of movement; FIG. 4*b* illustrates a typical physiotherapy maneuver, 3D octet-like course; FIGS. 4*c* to 4*f* represent various sets of various maneuvers made by a plurality of Allowed Movements of the head and neck of the present invention.

SUMMARY OF THE INVENTION

Figure 1:
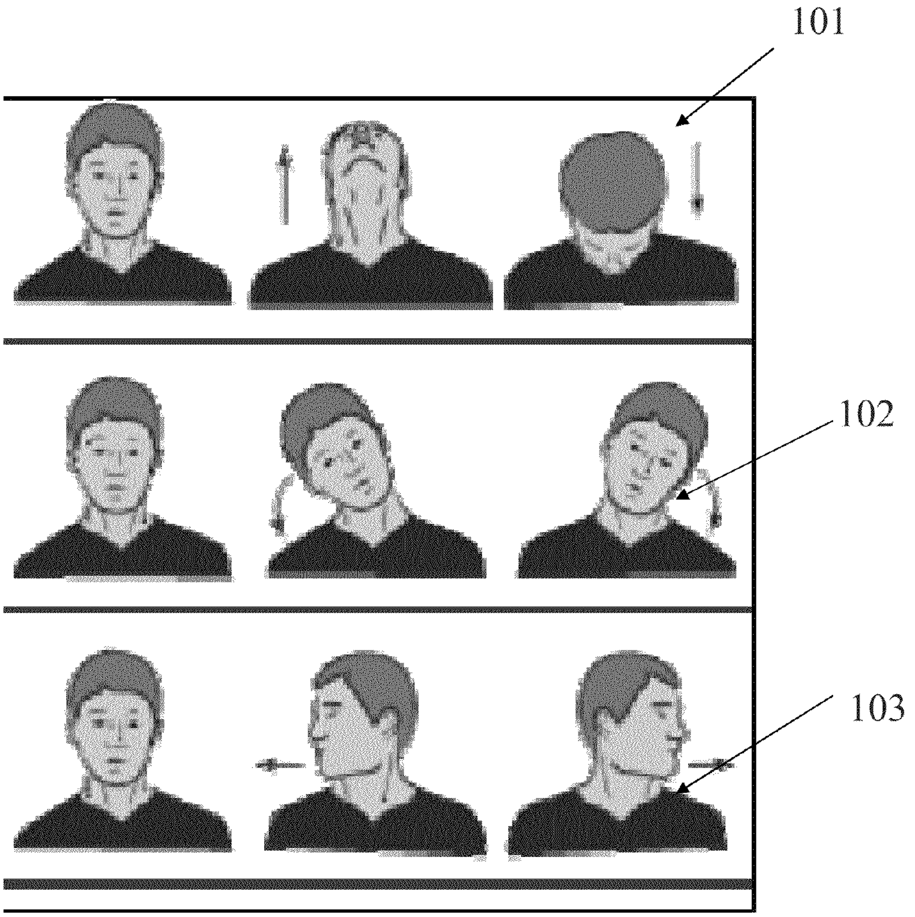
Figure 2A:
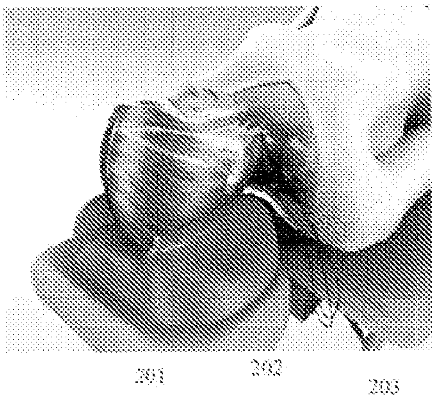
FIG. 2*a* illustrates an embodiment of the invention including cradle 201, partially filled with viscous fluid, platform 202 supporting the cradle and moved by motors in three planes, and EMG electrodes 203, used for research purposes, to determine the optimal course of treatment.
Figure 2B:
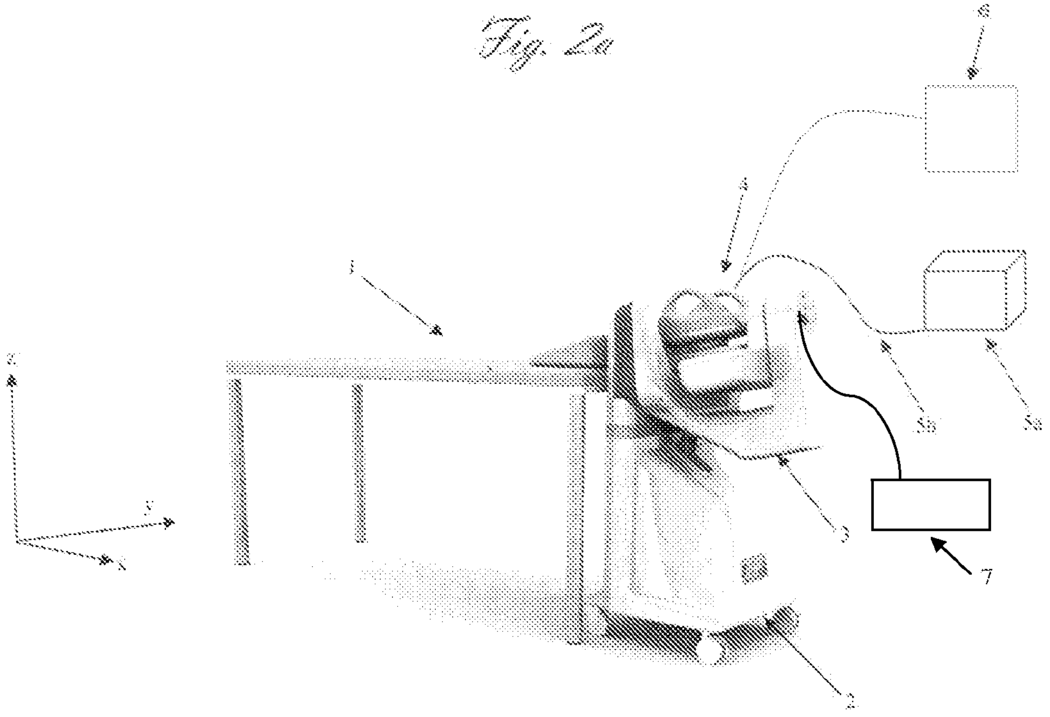
FIG. 2*b* illustrates a device according to one embodiment of the invention, wherein 1, 2, 3, 5*a*, 5*b*,6, and 7 denote respectively, the standard treatment table (upon which the person undergoing treatment rests on), portable base, motion system, cradle members of the device, means for playing music or virtual reality during treatment, means for providing the music or virtual reality to the patient, means for detecting at least one parameter related to at least one condition selected from the group consisting of the patient's medical condition, the patient's physiological condition, and the patient's emotional condition, and means for online or offline processing of said parameters.
Figure 3:
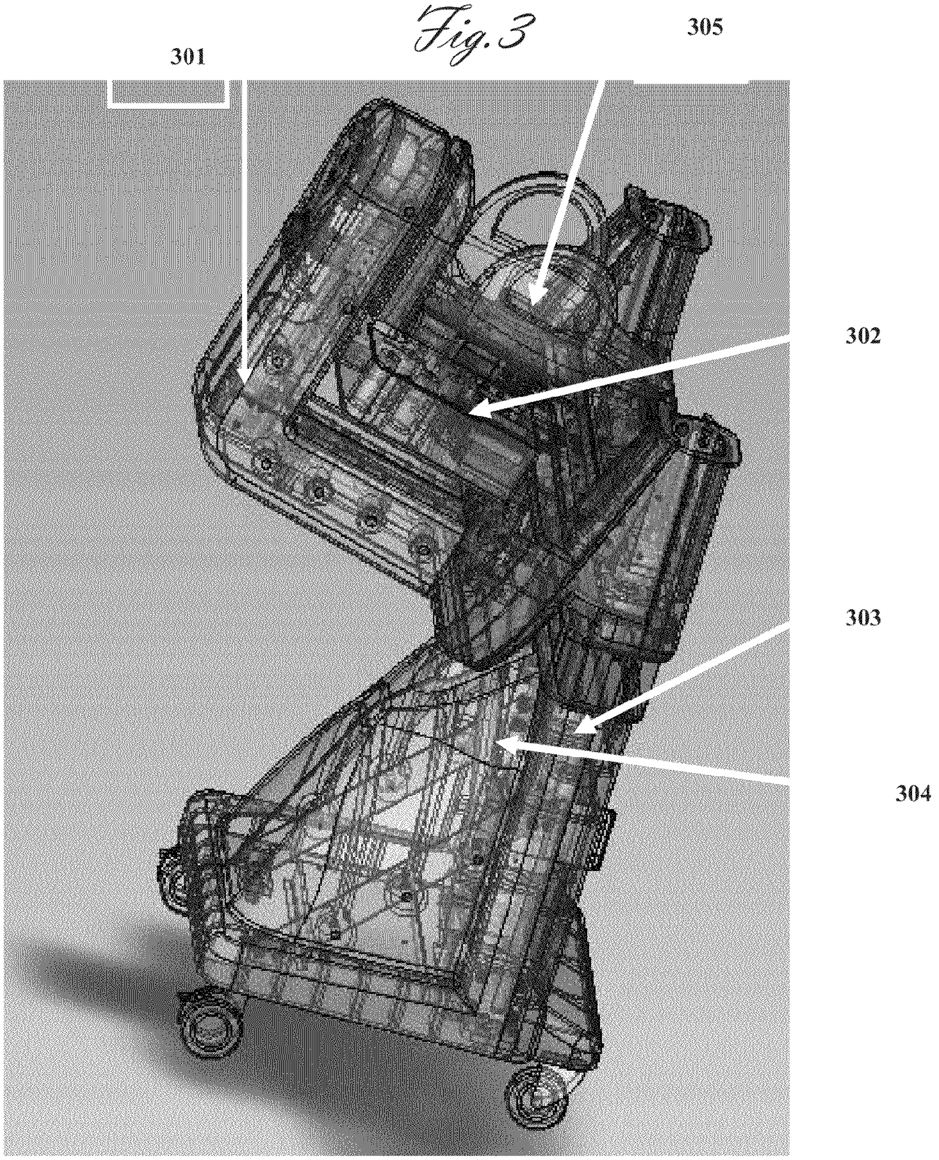
FIG. 3 illustrates an embodiment of the invention showing the two motors 301 (Horizontal) and 302 (Coronal) and two linear actuators 303, and 304 (Sagittal) which move the Cradle 305, in the three planes.

It is one object of the invention to disclose an apparatus for treating patient body or an organ thereof (the treated organ), especially his/her head and neck, by controllably maneuvering said treated organ. The device comprising inter alia the following modules: (a) cradle adapted for holding said treated organ stably and comfortably; and (b), a maneuverable platform upon which said cradle rests, comprising maneuvering means adapted for rotating the platform in the Sagittal, Coronal, Horizontal planes or in any combination of the planes thereof, for a predetermined duration. The apparatus is designed to provide a maneuver which is characterized by parameters selected inter alia from the Allowed Movements as defined hereinafter.

It is another object of the invention to disclose an apparatus as defined above, additionally comprises a processing means for either online or offline controlling or determining said parameters.

It is another object of the invention to disclose an apparatus as in any of the above, defined above, additionally comprises at least one detecting means adapted to obtain one or more parameters related to said patient medical, physiological, and/or emotional condition.

It is another object of the invention to disclose an apparatus as in any of the above, defined above, wherein said at least one detecting means is selected from a group consisting inter alia of EMG, EKG, GSR or a combination thereof.

It is another object of the invention to play relaxing music during the treatment.

It is another object of the invention to play virtual reality during the treatment.

It is another object of the invention to disclose an apparatus as in any of the above, wherein said at least one detecting means is operable in a feedback or bio-feedback mode, i.e., is in a feedback manner interconnected with the maneuverable platform such that at least a portion of said maneuver parameters is either online or offline updated.

It is another object of the invention to disclose an apparatus as in any of the above, additionally comprises at least one reporting means, adapted to either online or offline report said patient condition, said report is provided either to a remote module or to an adjacent module.

It is another object of the invention to disclose a method for treating patient body or an organ thereof (the treated organ), especially his/her head and neck. The method comprises steps selected inter alia from (a) placing the treated organ on a manipulable cradle; and (b), controllably maneuvering said cradle, either in a direct or indirect manner, in the Sagittal, Coronal, Horizontal planes or in any combination of the planes thereof for a predetermined duration. The aforesaid maneuvering step or steps is characterized by parameters selected from the Allowed Movements.

It is another object of the invention to wherein the aforesaid method additionally comprising at least one step of detecting either online or offline, either pre-operation of while operation, the condition of said patient or said treated organ, especially wherein said detecting is provided by means of EMG, EKG, GSR or a combination thereof. The method is possibly comprising step/steps (c) in a feedback manner interconnecting said manipulatable cradle with said detecting means and step/steps (d), either online or offline, either pre-operation of while operation updating at least a portion of said maneuver parameters.

It is another object of the invention to disclose a method for increasing Functional health status SF-36 score of a patient, comprising inter alia step or steps of manipulating the body of said patient or an organ thereof in the Allowed Movements, wherein said SF-36 is improved by at least 10%, when compared with a control group which has not undergone said manipulations.

It is another object of the invention to disclose a method for decreasing HIT (Headache Impact Test score) and especially HIT-6 of a patient. This method comprises inter alia step or steps of manipulating the body of said patient or an organ thereof in the Allowed Movements, wherein said HIT-6 decrease said score in at least one stage, when compared with a control group which has not undergone said manipulations.

It is another object of the invention to disclose a method for decreasing MIDAS (Migraine Disability Assessment Questionnaire), score of a patient. The method comprising step or steps of, e.g., manipulating the body of said patient or an organ thereof in the Allowed Movements, wherein said MIDAS decrease said score in at least one stage, when compared with a control group which has not undergone said manipulations.

It is another object of the invention to disclose a method for decreasing VAS/NRS: Visual Analog Scale/Numerical (10-point) Rating Scale. This method comprises the various steps of manipulating the body of said patient or an organ thereof in the Allowed Movements, wherein said VAS/NRS score decreases by at least 20%, when compared with a control group which has not undergone said manipulations.

It is another object of the invention to disclose a method for increasing Short Musculoskeletal Function Assessment ((S) MFA). The method comprising manipulating the body of said patient or an organ thereof in the Allowed Movements, wherein said (S)MFA score increases in at least 10% when compared with a control group which has not undergone said manipulations.

It is another object of the invention to disclose a method as defined in any of the above, being used in treating headaches especially migraines, myofascial, headache, tension-type headache and post traumatic headache.

It is another object of the invention to disclose a method as defined in any of the above, being used in treating neck pains especially whiplash, muscular pain, cervical disc-herniation/protrusion associated with neck and arm pain, over-tension of the neck muscles and neck movement disorders.

It is another object of the invention to disclose a method as defined in any of the above, being used to achieve relaxation of the organs selected from a group of head, neck and shoulders after effort and stress.

It is another object of the invention to disclose a method as defined in any of the above, being used to improve flexibility of neck muscles; treating patients with sleep disorder; reducing post-traumatic neck pain; increasing neck muscle mass; improving neck ROM; and rehabilitating natural neck movements post injury.

It is still another object of the invention to disclose a method for decreasing EPS (Epworth Sleepiness Scale) score. This method comprising, in a non-limiting manner, steps of manipulating the body of said patient or an organ thereof in the Allowed Movements, wherein said ROM decreases by at least 10% when compared with a control group which has not undergone said manipulations.

It is lastly object of the invention to disclose a method for decreasing NDI: Neck Disability Index. The method comprises steps of manipulating the body of said patient or an organ thereof in the Allowed Movements, wherein said ROM decreases by at least 10% when compared with a control group which has not undergone said manipulations.

DETAILED DESCRIPTION OF PREFERRED EMBODIMENTS

The following description is provided, alongside all chapters of the present invention, so as to enable any person skilled in the art to make use of said invention and sets forth the best modes contemplated by the inventor of carrying out this invention. Various modifications, however, is adapted to remain apparent to those skilled in the art, since the generic principles of the present invention have been defined specifically to provide a dynamic cradle.

The term 'plurality' refers hereinafter to any integer number equal or higher 1, e.g., 2 to 10, especially 2 to 4.

The term 'about' refers hereinafter to a value being up to ±25% of the defined measure.

The term 'EMG sensor' refers hereinafter to surface electromyographic sensor, this being an electrical sensor adapted for measurement of compound muscle action potential, which is correlated to the degree of muscle activation.

The term 'cradle' refers to a supporting means, selected in a non-limiting manner for cradles, pillows, headrests, cushions, puffs, mattresses etc.

In essence the proposed device is a computerized neck mobilization device, which is controlled by muscle feedback. It supports natural neck lordosis. The dynamic cradle is a multi-layered pillow, which is filled with liquid/viscous material. The person undergoing treatment rests his or her head within a recess in the cradle while lying down, either prone or supine. In the course of the treatment the head is caused to perform a 3D oscillatory movement at a very slow velocity (e.g., 0.3 through 3 deg/sec) by means of motors adapted to move a platform, on which the cradle rests, in three axes. This slow movement is adapted to lengthen and relax over-contracted neck muscles. It is adapted to gradually abolish abnormal neck muscle contraction patterns.

A computer controls the movement of the motorized platform upon which the cradle rests.

In one embodiment of the invention this computer provides movement of the head described in the following table, in which the angle of the head is defined by the vector of movement angles in the Sagittal, Coronal, and Horizontal planes, denoted (S, C, H), where S is the Sagittal angle in degrees, C is the Coronal angle in degrees, and H is the Horizontal angle in degrees, and where in all planes 0° is the position of the un-tilted head:

TABLE 1

Basic Movement Cycle and Allowable Movements

| Step | Allowable Movement | Start Angle | End Angle |
|---|---|---|---|
| 1. | Sagittal flexion | (0°, 0°, 0°) | (Up to 70°, 0°, 0°) |
| 2. | Sagittal return | (Up to 70°, 0°, 0°) | (0°, 0°, 0°) |
| 3. | Coronal tilt right | (0°, 0°, 0°) | (0°, Up to 45°, 0°) |
| 4. | Coronal return right | (0°, Up to 45°, 0°) | (0°, 0°, 0°) |
| 5. | Coronal tilt left | (0°, 0°, 0°) | (0°, Up to −45°, 0°) |
| 6. | Coronal return left | (0°, Up to −45°, 0°) | (0°, 0°, 0°) |
| 7. | Horizontal rotation right | (0°, 0°, 0°) | (0°, 0°, Up to 45°) |
| 8. | Horizontal return right | (0°, 0°, Up to 45°) | (0°, 0°, 0°) |
| 9. | Horizontal rotation left | (0°, 0°, 0°) | (0°, 0°, Up to −45°) |
| 10. | Horizontal return left | (0°, 0°, Up to −45°) | (0°, 0°, 0°) |

It is in the scope of the invention wherein the patent's body or an organ thereof is manipulated in a set of (i) allowed movement, (ii) start angles, and (iii) end angles; Sagittal flexion, (0°, 0°, 0°), (Up to 70°, 0°, 0°), respectively; Sagittal return (Up to 70°, 0°, 0°), (0°, 0°, 0°); Coronal tilt right, (0°, 0°, 0°), (0°, Up to 45°, 0°); Coronal return right, (0°, Up to 45°, 0°), (0°, 0°, 0°); Coronal tilt left, (0°, 0°, 0°), (0°, Up to −45°, 0°); Coronal return left, (0°, Up to −45°, 0°), (0°, 0°, 0°); Horizontal rotation right, (0°, 0°, 0°), (0°, 0°, Up to 45°); Horizontal return right, (0°, 0°, Up to 45°), (0°, 0°, 0°); Horizontal rotation left, (0°, 0°, 0°), (0°, 0°, Up to −45°); Horizontal return left, (0°, 0°, Up to −45°), (0°, 0°, 0°), respectively, refers in the present invention as 'Allowed Movements'.

In 'feedback mode' the computer receives feedback signals from EMG sensors on the patient's shoulder girdle neck and/or facial muscles, to optimize a personal unique treatment of the head and neck in three dimensional space and time. The biofeedback uses electromyography, involving electrodes which monitor the compound active muscles action potential.

The pattern movement optimization of is established through a mathematical algorithm. Once the following parameters: 3D diverse positions, motion sequences, frequencies and movement timing are optimized in all three planes; this data is stored for further treatments.

Due to the technology used, the patient undergoes a relaxing "zero gravity" floating experience, which leads to profound muscle relaxation, including relaxation of neck muscles as well as facial and mastication muscles.

This dynamic cradle is useful for the treatment of pain especially head and neck pain syndromes such as migraine, and other headaches: tension type, post traumatic, cervicogenic, and myofascial headache, as well as neck pain, such as whiplash injury and muscle over-contraction.

Moreover, this dynamic cradle is useful for the treatment of ROM dysfunctions, by improving patient's ROM and neck muscle flexibility; rehabilitation and relaxation of shoulder and neck muscles over-contraction, e.g., after sport activity and/or other injuries, and whole body relaxation. Besides, while opposing the cradle movement one can increase his or her muscle bulk & strength.

In one embodiment of the invention, vestibular physical therapy is provided for treatment of patients with Benign Paroxysmal Positional Vertigo.

In addition, this dynamic cradle is useful for treating sleep disorders; and cervical disc-herniation/protrusion associated with neck and arm pain and osteoarthritis coupled with arm pain. According to one embodiment of the invention, it produces a kneading action similar, but markedly superior to that achieved by physical therapist neck mobilization.

While the invention is susceptible to various modifications and alternative forms, specific embodiments thereof have been shown by way of example in the drawings and is adapted to herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

According to yet another preferred embodiment of the present invention, a cradle is provided that conforms to the shape of the human head, neck and shoulders. The cradle rests upon a platform, which in turn may be moved in three dimensions by a plurality of motors. These motors are controlled by a computer actuating electronics adapted to do so.

In another embodiment of the invention a series of electromyographic sensors are used to provide feedback to the computer algorithm controlling the cradle's movements. By means of this feedback, movement of the motorized platform is optimized in order to provide the maximum level of muscle relaxation as indicated by the electromyographic signal.

In another preferred embodiment of the invention, the optimal 3D diverse positions, motion sequences, frequencies and timing information gleaned from each individual feedback and saved by the computer program for future use.

In another embodiment of the invention, GSR and EKG signals are also used as feedback signals to inform operation of the computer algorithm, and achieve relaxation parameters of the whole body, and not only the treated areas.

In another embodiment of the invention, an additional supporting cradle is provided for neck lordosis, which may be separately adjustable.

In another preferred embodiment, the head is contained in a depression of at least 10 by 10 centimeters, such that in motions of rotation, flexion and lateral bending or tilting, the head is adapted to not slip from its place and the motion due to a given movement is adapted to therefore be predictable and repeatable.

In another preferred embodiment the platform movement-frequency is adapted to be between about 0.03 Hertz to about 0.2 Hertz.

In another preferred embodiment, the head tilt angle is adapted to be fixed to an accuracy of 1 degree.

In another embodiment of the invention a Faraday cage is adapted to be provided around the motor to eliminate any interference between the motor and the electromyographic sensors.

In another embodiment of the invention the user or operator is able to limit the head lifting/manipulating angle by means of an external switch.

In another preferred embodiment a preliminary test program is performed on the subject, to determine the maximum motion angle at each plane (See table 1) and any of the three planes combined motions. The preliminary test mode allows the optimization of safe and optimal treatment plan.

In another preferred embodiment a menu of different movement courses or cycles is available, each tailored to deal most effectively with a different type of patient.

In another preferred embodiment each plane is capable of independent activation.

In another preferred embodiment feedback from electromyographic devices is used to optimize the 3D diverse positions, motion sequences, frequencies and timing of the cradle movement.

In another preferred embodiment the upper body may be raised by a further part of the cradle to between about 15 and about 20 degrees.

In another embodiment of the invention, relaxing music is played during the treatment.

In another embodiment of the invention, either 2D or 3D virtual reality is played or displayed during at least portions of the treatment.

In another embodiment of the invention, the cradle may be heated or cooled.

In another embodiment of the invention, the platform upon which the cradle rests is attached to the bed upon which the person undergoing treatment rests.

The term "SF-36" was constructed to survey health status in the Medical Outcomes Study, see for example in http://www.mcw.edu/midas/health/SF-36.html. The SF-36 was designed for use in clinical practice and research, health policy evaluations, and general population surveys. The SF-36 includes one multi-item scale that assesses eight health concepts: 1) limitations in physical activities because of health problems; 2) limitations in social activities because of physical or emotional problems; 3) limitations in usual role activities because of physical health problems; 4) bodily pain; 5) general mental health (psychological distress and well-being); 6) limitations in usual role activities because of emotional problems; 7) vitality (energy and fatigue); and 8) general health perceptions. The survey was constructed for self-administration by persons 14 years of age and older, and for administration by a trained interviewer in person or by telephone. The history of the development of the SF-36, the origin of specific items, and the logic underlying their selection are summarized. The content and features of the SF-36 are compared with the 20-item Medical Outcomes Study short-form.

The term "Headache Impact Test (HIT)" is a tool used to measure the impact headaches have on the ability to function on the job, at school, at home and in social situations, see for example in http://www.headachetest.com/HIT6/PDFS/English.pdf. The patient's score shows the effect that headaches have on normal daily life and on the ability to function. HIT was developed by an international team of headache experts from neurology and primary care medicine in collaboration with the psychometricians who developed the SF-36 health assessment tool. The term "HIT-6" is a short-form version of the HIT, using just six items to capture the effect of headache and its treatment on an individual's functional status and wellbeing see for example in http://www.qualitymetric.com/products/hit6.aspx. HIT-6 is useful both for screening and for monitoring change in disease impact.

The term "Migraine Disability Assessment Questionnaire (MIDAS)" is a questionnaire that measures headache-related disability simply and easily by counting the number of days of lost and limited activity due to migraine, see for example in http://www.midasmigraine.net/edu/about.asp. Activities are classed into three areas: (1) Paid work and education (school/college); (2) Household work (unpaid work such as housework, shopping and caring for children and others); (3) Family, social and leisure activities. MIDAS was developed to improve migraine care by helping physicians to identify sufferers most severely affected by their migraine and, therefore, most in need of care. The MIDAS approach increases the likelihood of patients receiving the right treatment, the first time they visit their physician about migraine.

The term "Visual Analog Scale/Numerical Rating Scale (VAS/NRS)" is a scale that helps patients describes their pain, see for example in http://www.nccn.org/patients/patient_gls/_english/_pain/2_assessment.asp. The pain scale is commonly used to describe the intensity of the pain or how much pain the patient is feeling. On the numerical rating scale, the person is asked to identify how much pain they are having by choosing a number from 0 (no pain) to 10 (the worst pain imaginable). The visual analog scale is a straight line with the left end of the line representing no pain and the right end of the line representing the worst pain. Patients are asked to mark on the line where they think their pain is.

The term "(Short) Musculoskeletal Function Assessment ((S)MFA)" evaluates the health status of patients with musculoskeletal disorders of the extremities, including patients with fractures and soft tissue injuries, repetitive motion disorders, osteoarthritis or rheumatoid arthritis, see for example http://www.ortho.umn.edu/img/assets/12487/instruc.doc. It describes patient functioning, assesses outcomes of surgical interventions and clinical trials, and monitors patients' functional status over time The term "Range of motion (ROM)" is a measurement of the achievable distance between the flexed position and the extended position of a particular joint or muscle group, see for example in http://en.wikipedia.org/wiki/Range_of_motion. The act of attempting to increase this distance through therapeutic exercises (range of motion therapy—stretching from flexion to extension for physiological gain) is also sometimes called range of motion. It is in the scope of the invention wherein success is recorded by improving of 10% in range of motion. Such an improvement is recorded, e.g., by factorizing the five main movements: Sagittal plane, Horizontal plane (left and right), and Coronal (left and right) plane.

The term "Neck Disability Index (NDI)" is a questionnaire that assesses the neck pain complaints, see for example in http://www.painworld.zip.com.au/articles/tools/Neck%20Disability%20Index.pdf. It is designed to enable the understanding of how much the neck pain has affected the ability to manage everyday activities.

The term "Epworth Sleepiness Scale (EPS)" is a scale which is used to determine the level of daytime sleepiness, see for example in http://www.umm.edu/sleep/epworth_sleep.html. A score of 10 or more is considered sleepy. A score of 18 or more is very sleepy. If you score 10 or more on this test, you should consider whether you are obtaining adequate sleep, need to improve your sleep hygiene and/or need to see a sleep specialist.

Figure 4A:
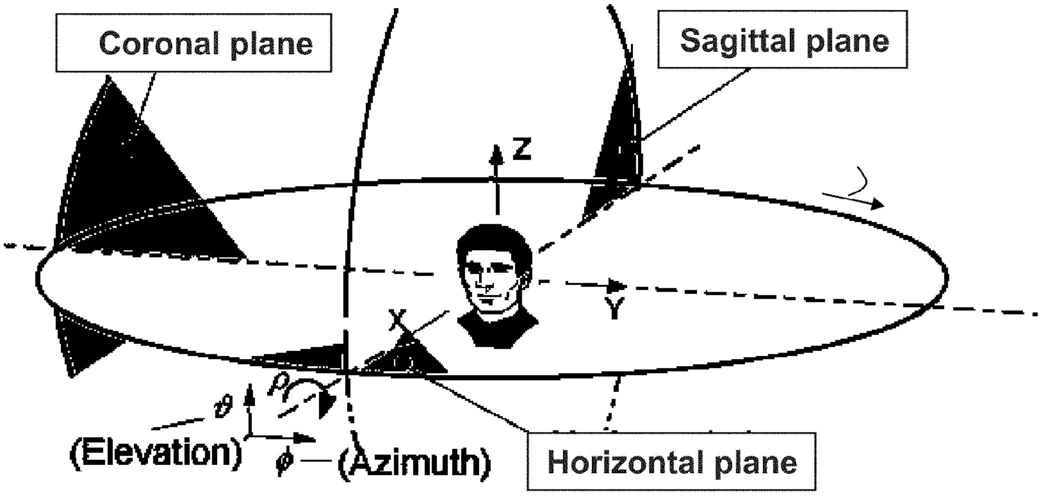
FIGS. 4*a* to 4*f* illustrate in an out-of-scale manner various lobular two and three dimensional maneuvers according to a set of possible embodiment of the present invention.
Figure 4B:
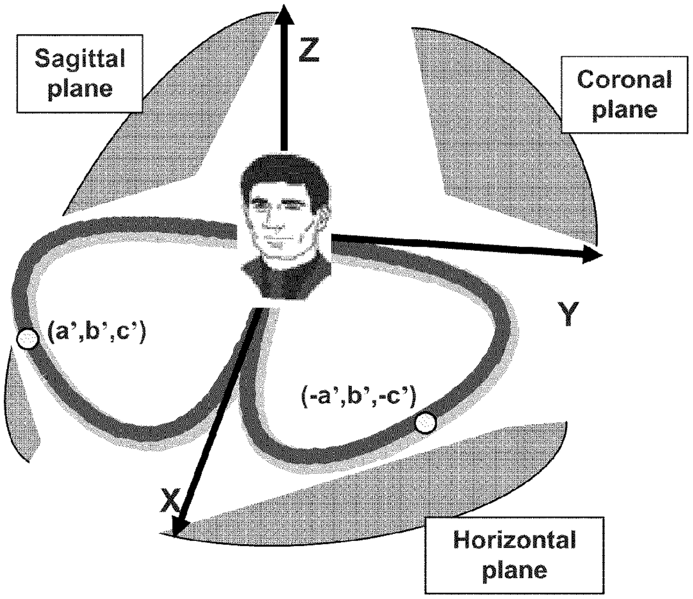
Figure 4C:
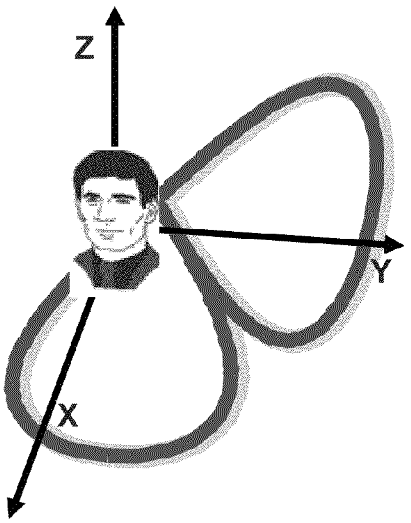
Figure 4D:
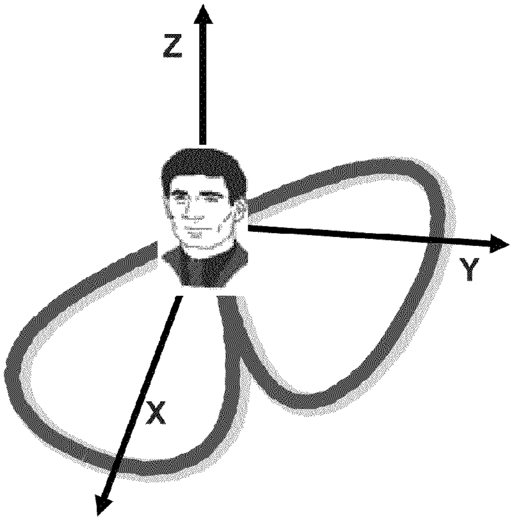
Figure 4E:
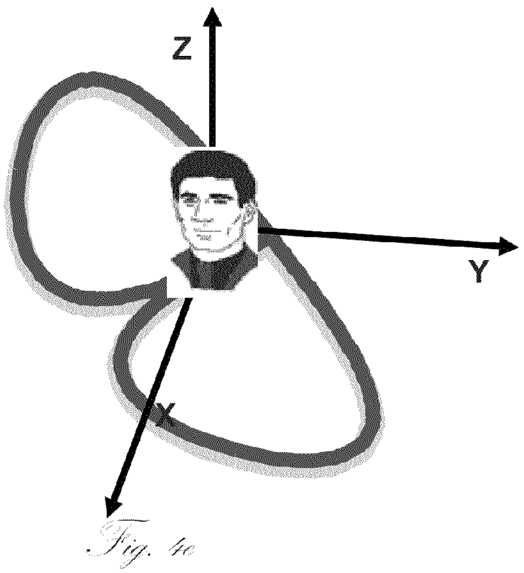
Figure 4F:
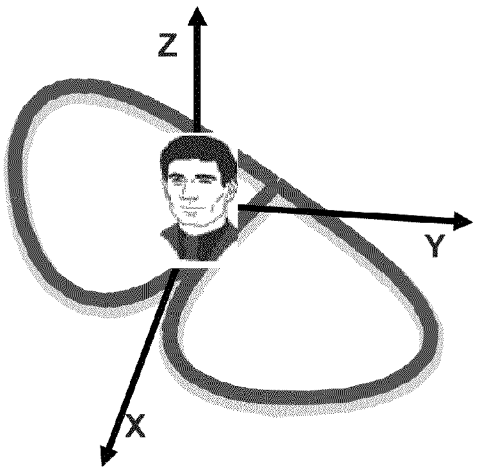

Reference is now made to FIGS. 4*a* to 4*f*, illustrating in an out-of scale manner the direction in which the treated organ is maneuvered. FIG. 4*a* illustrates an even 8-like track (here, a clockwise direction 401). This lobular maneuver is provided in a two dimensional and/or a three dimensional manner here a loop-like continuous movement along the Sagittal plane. FIG. 4*b* depicts similar 8-like track, here, along a counter-clockwise direction 402. FIGS. 4*c*-4*f* depict similar 8-like continuous movement along various planes. It is acknowledged in this respect that uneven 8-like (with one extended lob) continuous movements along all Sagittal, Horizontal, and Coronal planes are possible.

This 2D and/or 3D maneuver is provided in a continuous or interrupted manner, in a spontaneous, feedbacked and/or predetermined manner. It is in the scope of the invention wherein the aforesaid 3D movement is provided with six degrees of freedom (DFs), especially wherein the motion is characterized by a continuous passive motion in a 6-DFs lobed maneuver.

Figure 5A:
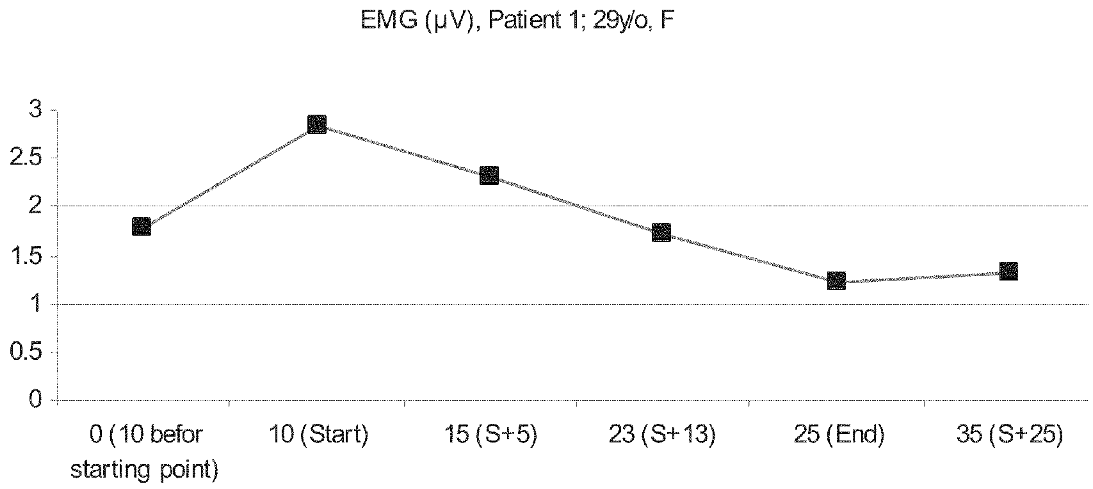
FIGS. 5*a* and 5*b* illustrates EMG results in health and sick patients, respectively, before, while and after treatment by the device and methods of the invention.
Figure 5B:
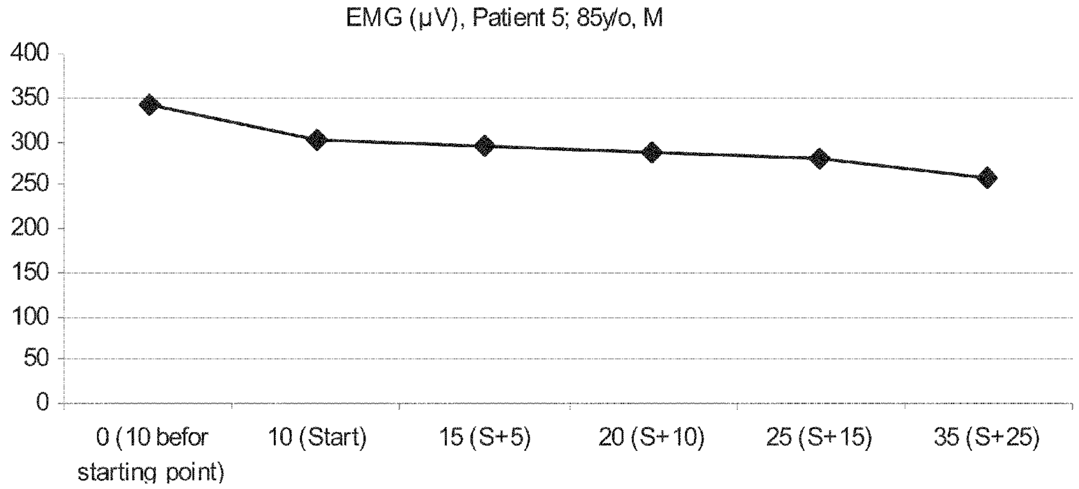

Reference is now made to FIGS. 5*a* and 5*b*, presenting examples of EMG results in a control patient (a healthy female aged 30 years) and an 85 years old male patient with tension type headaches (TTH), respectively. EMG values increase at the initial 10 minutes of resting the head on a cradle (see member 201 above). By actuating the maneuverable platform upon which the cradle rests, by maneuvering the head of the patient in Sagittal, plane in a set of Allowed Movements, EMG values significantly decreased from low value (2.5 μV) to even lower values (1.2 μV, 50% reduction for healthy control patient, FIG. 5*a*); and dramatically decreased in the TTH patient from very high values (350 μV) to lower values (250 μV, 30% reduction), respectively. Moreover, short-time after treatment effect is detected, see for example reduction of EMG from about 275 μV (25 min) at the termination of the treatment, to about 250 μV, 10 minutes after treatment has stopped. Similarly, a long-term treatment was obtained.

It is in the scope of the invention wherein the treatment is provided whereat the patient is laying in a relaxed manner, wherein minimal muscle tension (especially head and shoulder muscles) is provided.

It is also in the scope of the invention wherein the treatment is provided while (i) specific physiological data, e.g., EMG and ROM; and (ii) non-specific data, e.g., blood pressure, EKG (aka ECG; e.g., heart beat and beat to beat variability), galvanic skin response (GSR), is collected.

It is in the scope of the invention wherein the device and methods thereof are especially adapted for domestic or other out-of-clinic treatments.

It is still in the scope of the invention wherein the device is especially adapted to be provided with a 'learning mode', such that the caregiver and/or patient inputs parameters related to the maneuvers. The input is provided orally, physically (e.g., by utilizing caregiver's hands) or any other method.

It is lastly in the scope of the invention wherein the device is operated to reduce blood pressure (systole and/or diastole blood pressure), e.g., in 7.5% or more in respect to the pre-treatment basal level.

The invention claimed is:

1. An apparatus for treating a patient in need by controllably maneuvering at least one treated organ of said patient, comprising:

a cradle adapted for holding said treated organ stably and comfortably;

a maneuverable platform upon which said cradle rests, comprising means for maneuvering said platform adapted for rotating the platform, for a predetermined duration, in the Sagittal, Coronal, Horizontal planes in movements defined by vector of movement angles in at least one of the Sagittal, Coronal, and Horizontal planes, denoted (S, C, H), chosen from the group consisting of:

Sagittal flexion from a starting angle of (0°, 0°, 0°) to an end angle of (≦70°, 0°, 0°);

Sagittal return from a starting angle of (≦70°, 0°, 0°) to an end angle of (0°, 0°, 0°);

Coronal tilt right from a starting angle of (0°, 0°, 0°) to an end angle of (0°, ≦45°, 0°);

Coronal return right from a starting angle of (0°, ≦45°, 0°) to an end angle of (0°, 0°, 0°);

Coronal tilt left from a starting angle of (0°, 0°, 0°) to an end angle of (0°, −45°≦C≦0°, 0°);

Coronal return left from a starting angle of (0°, −45°≦C≦0°, 0°) to an end angle of (0°, 0°, 0°);

Horizontal rotation right from a starting angle of (0°, 0°, 0°) to an end angle of (0°, 0°, ≦45°);

Horizontal return right from a starting angle of (0°, 0°, ≦45°) to an end angle of (0°, 0°, 0°);

Horizontal rotation left from a starting angle of (0°, 0°, 0°) to an end angle of (0°, 0°, −45°≦H ≦0°);

Horizontal return left from a starting angle of (0°, 0°, −45°≦H ≦0°)to an end angle of (0°, 0°, 0°); and in any combination of the planes thereof; and, two motors and two linear actuators, said motors and actuators in mechanical connection with said maneuvering means to enable movement of said cradle in three planes means for detecting at least one parameter related to at least one condition selected from the group consisting of the patient's medical condition, the patient's physiological condition, and the patient's emotional condition;

wherein said detecting means is feedback interconnected with said maneuverable platform such that said at least one parameter and cradle movement is either online or offline updated.

2. The apparatus as defined in claim 1, wherein said treated organ is maneuvered in a lobular three dimensional manner.

3. The apparatus as defined in claim 1, additionally comprising means for processing for either online or offline controlling or determining said at least one parameter.

4. The apparatus as defined in claim 1, additionally comprising means for playing at least one selected from the group consisting of relaxing music, virtual reality (vision input), and virtual reality (audio input) during the treatment.

5. The apparatus as defined in claim 1, wherein said detecting means is selected from the group consisting of electromyography (EMG), electrocardiography (EKG), means for measuring galvanic skin response (GSR) and any combination thereof.

6. The apparatus as defined in claim 1, wherein said at least one treated organ comprises the head and neck.

7. The apparatus as defined in claim 1, further comprising means for reporting said condition in a manner chosen from the group consisting of offline reporting and online reporting to a module disposed in a location selected from the group consisting of adjacent to said apparatus and remote from said apparatus.

8. A method for treating a patient in need by controllably maneuvering at least one treated organ, wherein said method comprises:

placing said treated organ on a manipulatable cradle, said manipulatable cradle resting upon a maneuverable platform, said maneuverable platform in mechanical connection with at least one motor and at least one linear actuator, said at least one motor and at least one linear actuator disposed so as to enable movement of said cradle in three planes; and, controllably maneuvering said manipulatable cradle in a manner chosen from the group consisting of directly and indirectly, for a predetermined duration, in at least one of the Sagittal, Coronal, Horizontal planes in movements defined by vector of movement angles in the Sagittal, Coronal, and Horizontal planes, denoted (S, C, H), chosen from the group consisting of:

Sagittal flexion from a starting angle of (0°, 0°, 0°) to an end angle of (≦70°, 0°, 0°);

Sagittal return from a starting angle of (≦70°, 0°, 0°) to an end angle of (0°, 0°, 0°);

Coronal tilt right from a starting angle of (0°, 0°, 0°) to an end angle of (0°, ≦45°, 0°);

Coronal return right from a starting angle of (0°, ≦45°, 0°)to an end angle of (0°, 0°, 0°);

Coronal tilt left from a starting angle of (0°, 0°, 0°) to an end angle of (0°, −45°≦C ≦0°, 0°);

Coronal return left from a starting angle of (0°, −45°≦ C ≦0°,0°) to an end angle of (0°, 0°, 0°);

Horizontal rotation right from a starting angle of (0°, 0°, 0°) to an end angle of (0°, 0°, ≦45°);

Horizontal return right from a starting angle of (0°, 0°, ≦45°)to an end angle of (0°, 0°, 0°);

Horizontal rotation left from a starting angle of (0°, 0°, 0°)to an end angle of (0°, 0°, −45°≦H ≦0°);

Horizontal return left from a starting angle of (0°, 0°, −45°≦H ≦0°)to an end angle of (0°, 0°, 0°);

or in any combination thereof;

wherein said method further comprises steps of:

feedbacked interconnecting said manipulatable cradle with means for detecting at least one condition selected from the group consisting of the patient's medical condition, the patient's physiological condition, and the patient's emotional condition; and, updating at least a portion of said movements, said step of updating performed in a manner chosen from the group consisting of updating online and updating offline.

9. The method as defined in claim 8, additionally comprising at least one step of detecting, from a manner chosen from the group consisting of online and offline, at least one condition of said patient or said treated organ.

10. The method as defined in claim 9, wherein said step of detecting comprises at least one step selected from the group consisting of:

obtaining an electromyogram (EMG);

obtaining an electrocardiogram (EKG);

measuring galvanic skin response (GSR);

and any combination thereof.

11. The method as defined in claim 8, wherein said at least one organ is the head; further wherein said method comprising a step of treating headache pain.

12. The method as defined in claim 11, wherein said step of treating headache pain comprises treating pain due to a type of headache chosen from the group consisting of migraines, myofascial, muscular tension, nervous tension, and post traumatic pain.

13. The method as defined in claim 8, wherein said at least one organ is the neck; further wherein said method comprising a step of treating neck pain.

14. The method as defined in claim 13, wherein said step of treating neck pain comprises treating neck pain due to a cause chosen from the group consisting of whiplash, muscular pain, cervical disc-herniation and/or protrusion associated with neck and arm pain, over-tension of the neck muscles, and neck movement disorders.

15. The method as defined in claim 8, also adapted to achieve relaxation, after effort and stress, of at least one organ selected from the group consisting of head, neck and shoulders.

16. The method as defined in claim 8, further comprising a step of performing at least one therapeutic intervention chosen from the group consisting of improving neck muscle function; treating sleep disorders; increasing neck muscle bulk;

improving range of motion (ROM); and rehabilitating natural movements following injury.

17. The method as defined in claim 8, wherein said step of maneuvering comprises maneuvering in a lobular three dimensional manner.

* * * * *